US012011601B2

(12) United States Patent
Mower

(10) Patent No.: US 12,011,601 B2
(45) Date of Patent: Jun. 18, 2024

(54) METHOD AND APPARATUS FOR ELECTRICAL CURRENT THERAPY OF BIOLOGICAL TISSUE AND INSULIN RELEASE THEREFROM

(71) Applicant: ROCKY MOUNTAIN BIPHASIC, INC., South Minneapolis, MN (US)

(72) Inventor: Morton Mower, Denver, CO (US)

(73) Assignee: Rocky Mountain Biphasic, Inc., South Minneapolis, MN (US)

( * ) Notice: Subject to any disclaimer, the term of this patent is extended or adjusted under 35 U.S.C. 154(b) by 0 days.

(21) Appl. No.: 18/178,669

(22) Filed: Mar. 6, 2023

(65) Prior Publication Data

US 2023/0201606 A1 Jun. 29, 2023

Related U.S. Application Data

(63) Continuation of application No. 16/791,305, filed on Feb. 14, 2020, now abandoned.

(60) Provisional application No. 62/805,731, filed on Feb. 14, 2019.

(51) Int. Cl.
*A61B 5/145* (2006.01)
*A61N 1/05* (2006.01)
*A61N 1/372* (2006.01)

(52) U.S. Cl.
CPC .......... *A61N 1/372* (2013.01); *A61B 5/14503* (2013.01); *A61B 5/14532* (2013.01); *A61N 1/0507* (2013.01)

(58) Field of Classification Search
CPC .. A61N 1/372; A61N 1/0507; A61N 1/36007; A61B 5/14503; A61B 5/14532
See application file for complete search history.

(56) References Cited

U.S. PATENT DOCUMENTS

| 2009/0062881 A1* | 3/2009 | Gross | A61N 1/36007 607/40 |
| 2009/0131993 A1* | 5/2009 | Rousso | A61N 1/36017 607/2 |
| 2015/0360025 A1* | 12/2015 | Mower | A61N 1/32 607/116 |

FOREIGN PATENT DOCUMENTS

WO WO-2014070287 A1 * 5/2014 ......... A61N 1/36007

* cited by examiner

*Primary Examiner* — Ankit D Tejani
*Assistant Examiner* — Joshua Brendon Solomon
(74) *Attorney, Agent, or Firm* — DeWitt LLP; Brian R. Pollack, Esq.

(57) ABSTRACT

The present disclosure relates to a device for applying electrical stimulation to biological tissues. Specifically, the present disclosure is related to a device for applying anodal/cathodal biphasic electrical stimulation to beta cells of the pancreas. Through application of biphasic stimulation to beta cells of the pancreas, insulin secretion can be increased in an effort to overcome deficiencies associated with diabetic patients.

18 Claims, 13 Drawing Sheets

METHOD AND APPARATUS FOR ELECTRICAL CURRENT THERAPY OF BIOLOGICAL TISSUE AND INSULIN RELEASE THEREFROM

CROSS-REFERENCE TO RELATED APPLICATIONS

The present application is a continuation of and claims the benefit of priority to U.S. patent application Ser. No. 16/791,305, filed Feb. 14, 2020, which in turn claims the benefit of priority to U.S. Provisional Application No. 62/805,731, filed Feb. 14, 2019. Each of the foregoing patent applications, the teaching of which is incorporated by reference herein in its entirety for all purposes.

BACKGROUND

Field of the Disclosure

The present disclosure relates, generally, to a method and apparatus for the application of electrical stimulation to biological tissues. Specifically, the method and the apparatus of the present disclosure relate to electrically-stimulated release of insulin from the pancreas.

Description of the Related Art

Certain cells of the human body exhibit a membrane potential and some cells, including cardiac cells and cells of the nervous system, depolarize.

In some cases, such as the case of cardiac cells, the presence of a vigorous membrane potential functions to provide some protection against arrhythmias. As certain cells, such as cardiac cells, age, their membrane potential decreases and their function can deteriorate. In the case of cells of the myocardium, this manifests as slowed conduction of impulses and can lead to arrhythmias via re-entrant rhythms, early and late after-depolarizations, and decremental conduction.

In other cases, such as cells outside of the heart and the nervous system, depolarization of the cellular membrane and the function thereof is less appreciated. For example, depolarization of a beta cell within a pancreas initiates the secretion of insulin.

This occurs in two phases. A first phase lasts about five minutes and is initiated by closure of adenosine triphosphate (ATP)—sensitive potassium channels. Then, when the pancreas interacts with a glucose molecule, electrons are stripped from it and passed down the electron transport chain, thereby converting adenosine diphosphate (ADT) to ATP. This conversion leads to the closing of ATP-sensitive potassium channels and causes depolarization of beta cells of the pancreas. This phenomenon causes granules of insulin in the cytoplasm to migrate towards, and fuse with, the inner membrane of the cell. A pore then forms and the insulin is extruded into general circulation. A second phase of insulin production lasts from about 30 minutes to 2 hours. The second phase is related to calcium channels.

It is thought possible to exploit the electrical nature of beta cells in order to cause the release of insulin. The present disclosure, therefore, is directed to the application of biphasic electrical currents to the pancreas, responsive to glucose blood concentrations, in a way that controls the depolarization and repolarization of beta cells, thereby providing for controlled release of insulin.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a method for performing electrical current therapy on biological tissue, comprising applying, via processing circuitry, biphasic electrical current therapy to the biological tissue.

The present disclosure further relates to a method for performing electrical current therapy on biological tissue, comprising applying, via processing circuitry, biphasic electrical current therapy to the biological tissue, wherein the biological tissue includes pancreatic tissue and the method further comprises increasing insulin production of the pancreatic tissue by applying the biphasic electrical current therapy.

The present disclosure further relates to an apparatus for performing electrical current therapy on biological tissue, comprising at least one sensor, at least one electrode, and processing circuitry configured to acquire data from the at least one sensor, compare a value of the acquired data from the at least one sensor to a pre-determined threshold value, generate an electrical current based on the comparison of the value of the acquired data from the at least one sensor to the pre-determined threshold value, and apply the generated electrical current to the biological tissue via the at least one electrode, the applied generated electrical current corresponding to a voltage differential.

The foregoing has been provided by way of general introduction, and is not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

To accomplish the above, electrical stimulation is provided. Traditionally, monophasic cathodal pulses have been provided to beta cells of the pancreas. In a first way, depolarization of a beta cell can be induced with cathodal currents as such currents would reduce the membrane potential of the beta cell until the depolarization threshold is reached. Alternatively, in a second way, an anodal current, which can be related to insulin production, can be applied, though the role of anodal currents does not appear to have been previously investigated or appreciated.

According to an exemplary embodiment, placing anodal currents on the outside of cells increases the membrane potential and such an effect may last for a number of hours. The application of anodal currents also gives rise to an increased production of adenosine triphosphate (ATP) which is further used for the work of the cell.

According to another exemplary embodiment, electrical current therapy stimulates hormone production in endocrine tissues, which may lead to treatment of the various forms of diabetes, as addressed in the present disclosure. For example, types I and II diabetes are thought to have different etiologies. In some patients there is islet cell destruction with much less insulin production, while in others there may be a defect in the mechanism of insulin secretion. For example, the first defect that may be detected in pre-diabetes is a blunting of the first 5-minute surge of insulin secretion. Increasing the membrane potential of the beta cell by anodal, cathodal or biphasic current is thought to produce useful results by correcting this blunting.

The present disclosure, therefore, is directed to the application of biphasic electrical stimulation to biological tissues. In particular, the present disclosure is directed to the application of anodal/cathodal biphasic stimulation to beta cells of the pancreas for the inducement of insulin secretion.

Figure 1:
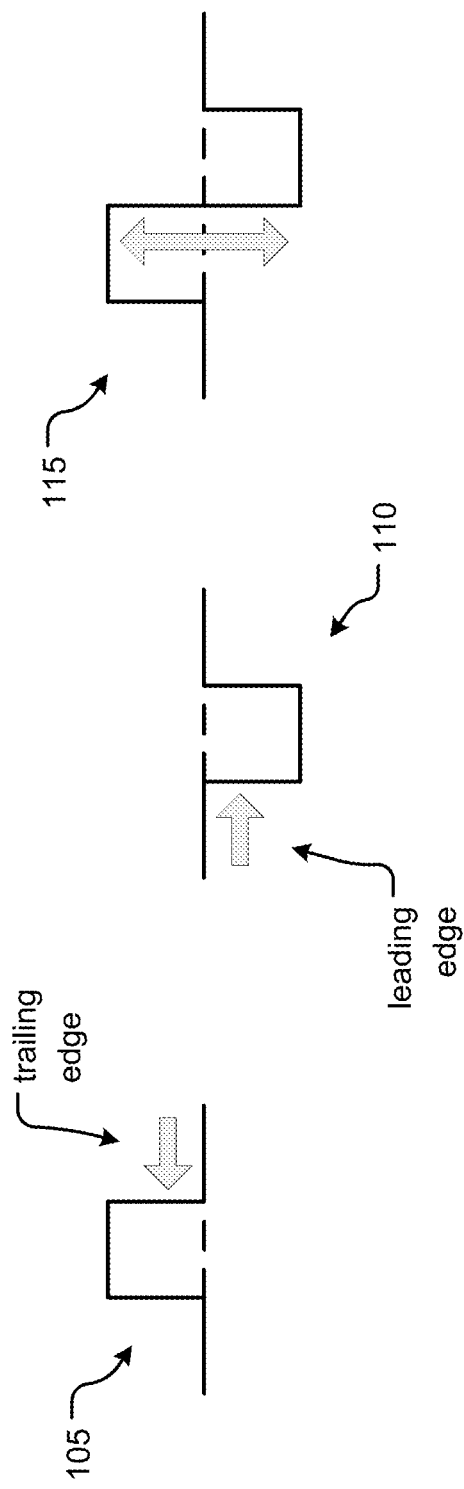
FIG. 1 is a schematic of waveforms for electrical current stimulation, according to an exemplary embodiment of the present disclosure.

Referring now to the Figures, FIG. 1 illustrates different waveforms that may be utilized for electrically stimulating biological tissue, such as beta cells of the pancreas. As shown in FIG. 1, anodal stimulation 105 and cathodal stimulation 110, which may be applied via different waveforms, may be utilized for electrically stimulating the biological tissue. Anodal stimulation 105 stimulates on the "break" or trailing edge of the pulse, whereas cathodal stimulation 110 is configured to operate on the "make" or leading edge of the pulse. Specifically, anodal stimulation 105 includes a pre-conditioning stage after which stimulation occurs on the trailing edge of the positive clock pulse (indicated by the arrow). On the other hand, cathodal stimulation 110 occurs on the leading edge of a negative clock pulse (indicated by the arrow). In addition, FIG. 1 describes a biphasic pulse 115 that creates a maximum total voltage difference between the positive peak and the negative peak greater than the anodal 105 or cathodal 110 stimulation pulses alone. It can be appreciated that combining the anodal pulse 105 and the cathodal pulse 110 doubles both the amplitude and duration of the stimulation, thus increasing the level of pre-conditioning (e.g., increase of membrane potential) and the strength of depolarization (e.g., speed at which the membrane potential crosses the stimulation threshold voltage). In other words, the peak to peak voltage of the biphasic stimulus 115, being of greater magnitude than the anodal 105 and cathodal 110 counterparts, drives the membrane potential swiftly past the stimulation threshold, thus giving the strongest possible depolarization pulse. The above-explanation is provided, for clarity, in terms of stimulation pulses. However, the principles described are applicable to any currents or waveforms used in electrical current therapy, whether stimulating or not, as would be understood by one of ordinary skill in the art.

Figure 2A:
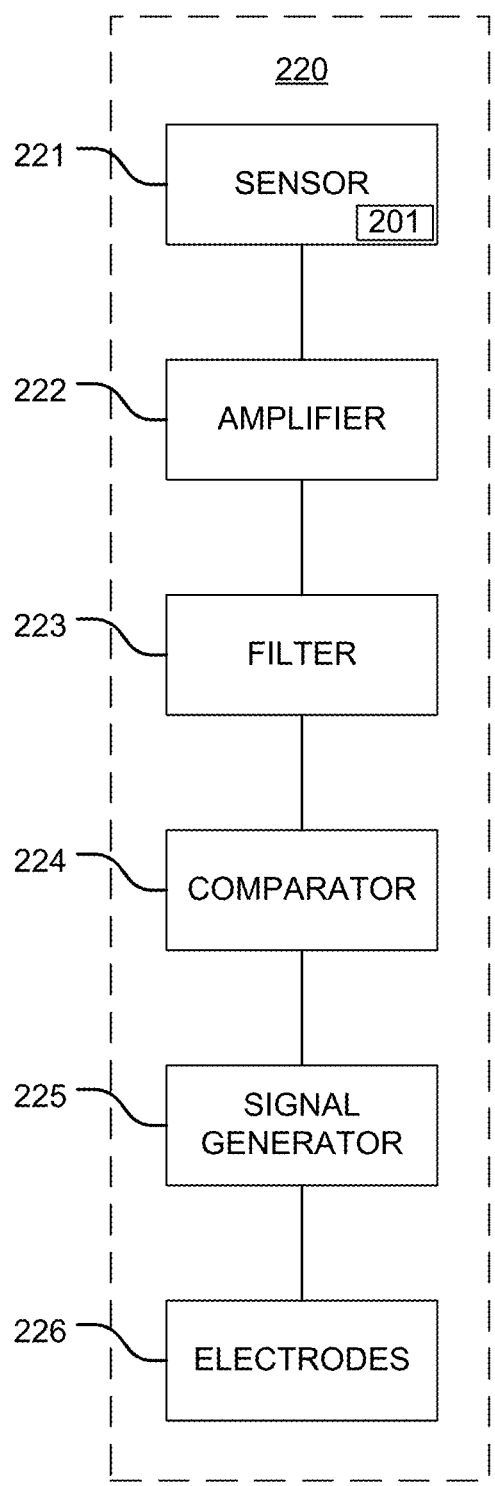
FIG. 2A is a block diagram of an apparatus for electrical stimulation, according to an exemplary embodiment of the present disclosure.
Figure 2B:
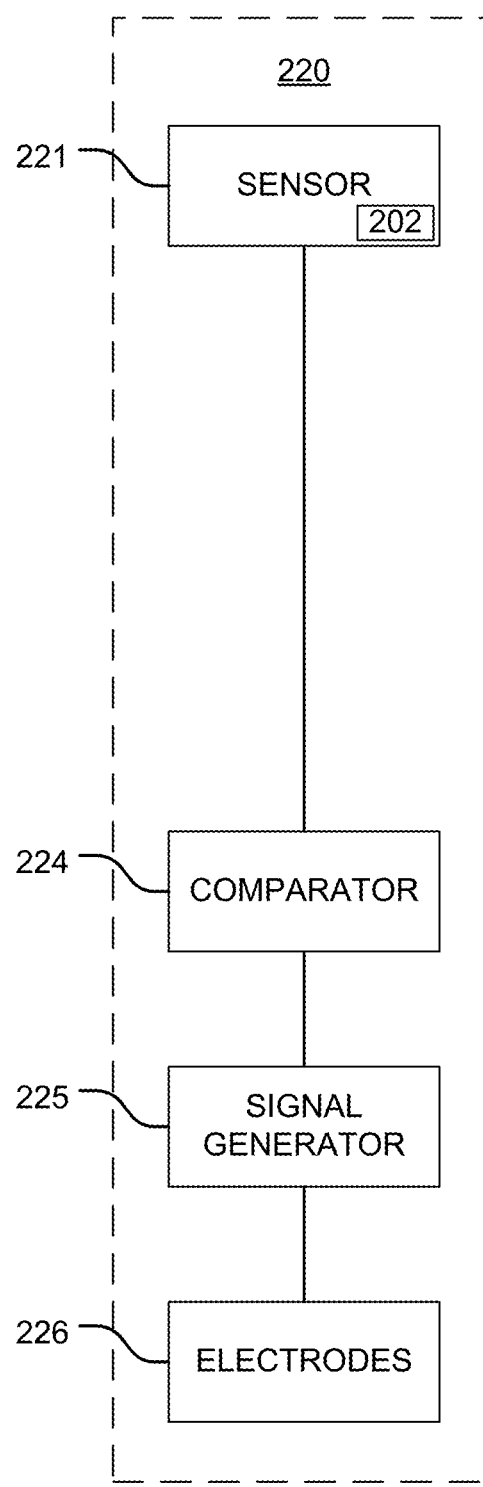
FIG. 2B is a block diagram of an apparatus for electrical stimulation, according to an exemplary embodiment of the present disclosure.

The electrical stimulation above can be provided to biological tissues, and beta cells of the pancreas, in particular, by a device described in FIG. 2A and FIG. 2B.

According to an embodiment of the present disclosure, a device as shown in FIG. 2A and FIG. 2B can be an implantable anodal/cathodal biphasic electrical stimulation device (ACBPS-D) 220. The ACBPS-D 220 can include at least one sensor 221, a low noise preamplifier 222, a filter 223, a comparator 224, a signal generator 225, and at least one electrode 226. Further to the above, the ACBPS-D 220, and components thereof, can include processing circuitry necessary to perform an intended function, including acquiring data, processing data, generating electrical stimuli, and controlling components of the ACBPS-D 220. In an example, the processing circuitry can be a low power consumption microcontroller that includes processing and memory circuits configured to control the overall operation of the ACBPS-D 220. For clarity, the processes of the ACBPS-D 220 will be described as a continuous method, however, it should be appreciated that FIG. 2A and FIG. 2B merely describe exemplary implementation of the ACBPS-D 220.

According to an embodiment, the at least one sensor 221 of the ACBPS-D 220 can include a voltage sensor 201 configured to determine a voltage potential, a glucose sensor 202, and an insulin sensor. For clarity, the ACBPS-D 220 will be described in FIG. 2A as including a voltage sensor 201 and in FIG. 2B as including a glucose sensor 202, though it can be appreciated that the two sensors can exist on the same device or separately and in addition to or excepting the insulin sensor.

With reference to FIG. 2A, in an exemplary embodiment, the at least one sensor 221 can be a voltage sensor 201 configured to detect and quantify a voltage potential of a biological tissue. In an example, the voltage sensor 201 is configured to detect a voltage potential across a cell membrane or from electrode locations within a biological tissue, or pancreas, in an example.

In an embodiment, data can be acquired from at least one voltage sensor 201 and amplified by an amplifier 222. In an example, the amplifier 222 can be a low noise preamplifier. Amplified data man be passed through a filter 223. In an example, the filter 223 can be a low noise filter configured to generate an appropriate signal. The appropriate signal can be a signal reflective of a voltage potential of a cell membrane, a biological tissue, and the like.

In an embodiment, the filtered data from the filter 223 can be provided to a comparator 224. The comparator 224 may implement a threshold detector to detect, for example, the voltage potential of a biological tissue. In one instance, the comparator 224 can provide feedback control by comparing an applied voltage potential with an intended voltage potential. In one instance, the comparator can compare a value of a membrane potential with a value of a depolarization threshold. The output of the comparator 244 can then be an input to a signal generator 225 configured to generate an electrical signal, the electrical signal being of a particular shape such as a square wave pulse, a saw tooth waveform, and the like. Moreover, the signal generator 225 can control the amplitude and frequency thereof. For instance, the signal generator 225 can generate a series of square wave pulses having an amplitude equivalent to any one of a range of voltages including 10 volts, 15 volts, 20 volts, and 25 volts.

In an embodiment, the signal from the signal generator 225 can be applied to electrodes 226 disposed at functional locations. As implemented, the generated signal can be biphasic electric current therapy.

According to an embodiment, the signal generator 225 can generate an electrical signal that is dependent upon an error determined by the comparator 224. For instance, the signal generator 225 can apply an electric signal of 10 volts when the error is 5% and the signal generator 225 can apply an electric signal of 25 volts when the error is 15%, in order to correct for the error.

With reference to FIG. 2B, in an embodiment, the at least one sensor 221 can be a biological sensor configured to detect and quantify a pre-determined biological molecule or similar. In an example, the biological sensor can be a glucose sensor 202 configured to detect glucose in blood of a patient. The glucose sensors 202 may be further configured to, via processing circuitry, quantify the concentration of glucose in the blood of the patient.

In an embodiment, the quantified data from the glucose sensor 202 can be provided to a comparator 224. The comparator 224 may implement a threshold detector to detect, for example, an elevated glucose concentration (i.e., blood sugar level). In an example, the comparator 224 may compare an analog signal from the glucose sensor 202 to a corresponding value of the threshold value. The output of the comparator 244 can be input to a signal generator 225 configured to generate a signal of a particular shape such as a square wave pulse, a saw tooth waveform or the like. In an embodiment, the comparator 244 may include an analog to digital converter. Moreover, the signal generator 225 can control the amplitude and frequency thereof. For instance, the signal generator 225 can generate a series of square wave pulses having an amplitude equivalent to any one of a range between 10 volts and 25 volts and including 10 volts, 15 volts, 20 volts, and 25 volts.

In an embodiment, the signal from the signal generator 225 can be applied to electrodes 226 disposed at functional locations. As implemented, the generated signal can be biphasic electric current therapy.

According to an embodiment, the signal generator 225 can generate an electrical signal that is dependent upon an error determined by the comparator 224. For instance, the signal generator 225 can apply an electric signal of 10 volts when the error is 5% and the signal generator 225 can apply an electric signal of 25 volts when the error is 15%, in order to correct for the error.

Though the above description refers to the ACBPS-D 202 as "implantable," the device may also be one that remains outside the body, (i.e., a device that is not implantable) instead having transcutaneous electrodes that are connected to the ACBPS-D 202. Therefore, the term "implantable" is to be considered as exemplary rather than limiting upon the present disclosure.

Introduced above, the application of biphasic current can increase the membrane potential of cells, thereby producing more ATP. Accordingly, the ACBPS-D 202 described above can be applied as a therapy in a variety of clinical situations. As related to diabetes, the effects of diabetes may be ameliorated by applying current to the pancreas. This can be achieved by passing a lead, or electrode, of an ACBPS-D 202 through the common bile duct, resting the lead within the head of the pancreas. Alternatively, a small screw-in lead can be directly applied to the pancreas through a tiny laparoscopic incision. This process can be used for applying current waveforms of many types, some stimulating production of insulin without affecting the normal endogenous secretion control mechanism, and other waveforms starting secretion by starting depolarization of the islet cells.

Furthermore, according to another exemplary embodiment, the above-described ACBPS-D 202 can be applied towards pancreatic tissues that are to be used for transplantation. Generally, such a tissue is placed in a "protected site", such as under the renal capsule. A problem that transplants surgeons commonly face is that of not knowing the viability of the cells, or how effectively they can produce insulin. However, biphasic current may be applied to the proposed tissue and the insulin produced thereby can be measured. Then, the cells may be stimulated to have a higher membrane potential which "up-regulates" insulin production and makes for a more active and better transplant. As one of ordinary skill would recognize, similar electrical current therapy may also be applied to virtually any endocrine tissue of the body.

Figure 3:
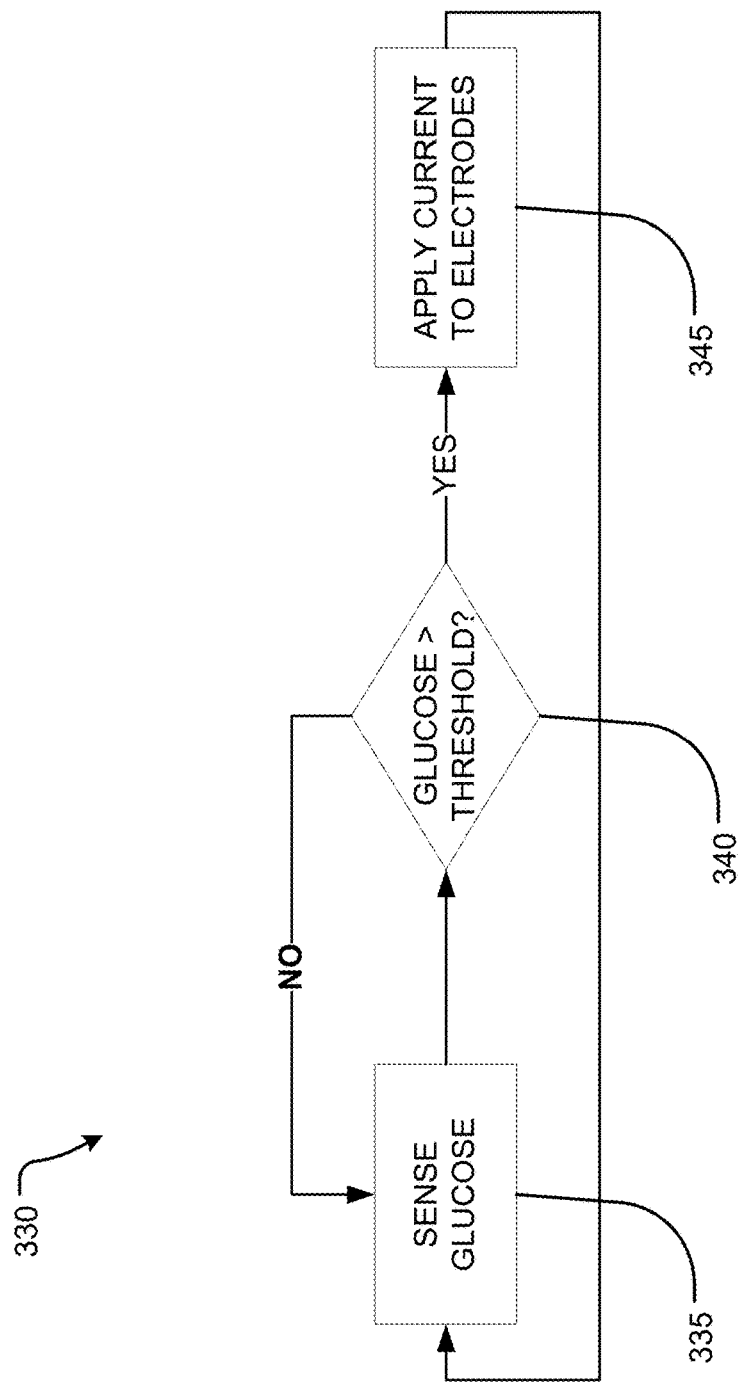
FIG. 3 is flow diagram of a method of an apparatus for electrical stimulation, according to an exemplary embodiment of the present disclosure.

Returning to the Figures, FIG. 3 provides a flow diagram of an exemplary method for applying electrical current therapy. While the method of FIG. 3 is directed to glucose sensing, it can be appreciated that, in view of FIG. 2A and FIG. 2B, glucose sensing and voltage sensing may occur concurrently or independently.

At step 335 of method 330, glucose in the blood of a patient can be sensed by a glucose sensor of the ACBPS-D. In an embodiment, the sensed glucose can be detected and quantified.

At step 340 of method 330, the quantified glucose data can be evaluated by a comparator to determine if the concentration of glucose in the blood of the patient is above a threshold at which insulin secretion would be required. If it is determined that the blood sugar level is too high at step 340, the ACBPS-D can deliver an electric current therapy (e.g., biphasic therapy) to the pancreas via electrodes at step 345 of method 330. If it is determined that the blood sugar level is below the threshold, the method 330 loops back to step 335 and glucose continues to be sensed.

In an embodiment, the comparator may evaluate, at step 340 of method 330, a current value of the quantified glucose data to a threshold to determine if an increase in insulin release, by electrical stimulation, is needed. Accordingly, the threshold may be a pre-determined blood glucose concentration threshold corresponding to a healthy blood glucose level in a patient. The healthy blood glucose level may be determined for each patient, individually, based on, among other things, age and life expectancy, conditions a person may have, cardiovascular disease or diabetes complications, hypoglycemia awareness, and duration of diabetes, if present. In an example, if the comparator determines, at step 340 of method 330, that the current value of the quantified glucose data is greater than the pre-determined blood glucose concentration threshold, then an electric current therapy may be generated and applied. For instance, the applied electric current therapy may be a pulsed therapy having a magnitude of 25 volts. In another instance, the applied electric current therapy may be a pulsed therapy having a variable magnitude between 10 volts and 25 volts, the variable magnitude being time dependent and based on a current deviation of the current value of the quantified glucose data and the pre-determined blood glucose concentration threshold.

The above described comparisons, performed by the comparator at step 340 of method 330, may be based on an analog signal corresponding to the current value of the quantified glucose data and an analog signal corresponding to the pre-determined blood glucose concentration threshold. To this end, it can be appreciated that processing circuitry of the ACBPS-D may be configured to evaluate a raw analog signal. Moreover, the processing circuitry of the ACBPS-D may be configured to convert each analog signal to standard units of glucose measurement according to a calibration curve, the converted signals then being compared to determine a deviation of the present glucose level.

As indicated, the electric current therapy applied to the pancreas at step 345 of method 330 may be based on a deviation of the current value of the quantified glucose data and the pre-determined blood glucose concentration threshold that is a target value for the patient. In example, if the deviation, represented by an error value, is approximately one standard deviation from the target value, an applied electric current therapy may have a magnitude of approximately one. Further, if the deviation is approximately two standard deviations from the target value, the applied electric current therapy may have a magnitude of approximately two. Of course, the above examples can be appreciated as merely exemplary of a system for graded responses to the comparison of the current blood glucose value and the target value. For instance, percentages, scaling, or any other suitable system for evaluating blood glucose levels and generating an appropriate electrical response may be considered without straying from the spirit of the present disclosure.

According to an embodiment, following application of electrical stimulation via the electrodes at step 345 of method 330, the method 330 returns to step 335 and glucose continues to be sensed until the comparator determines that the blood sugar level is equal to or minimally-below the pre-determined blood glucose concentration threshold.

For the sake of simplicity, the above discussion is presented as a sequence of steps that are performed serially. However, one of ordinary skill in the art would recognize that the steps of FIG. 3 may be performed in parallel such that glucose sensing at step 335 and electrical current therapy at step 345 may occur simultaneously. Other orders of performing these steps are also possible without departing from the scope of the present disclosure.

Non-Limiting Experimental Results

The effects of electrical stimulation on insulin release from rat insulinoma (INS-1) cells were evaluated. In brief, the anodal/cathodal biphasic stimulation (ACBPS) electrical waveform resulted in a voltage—and stimulation duration—dependent increase in insulin release. ACBPS elicited insulin release both in the presence and absence of glucose. Basal and BPS-induced insulin secretion can be inhibited by mitochondrial poisons and calcium channel blockers, indicating insulin release was dependent on ATP and the influx of calcium. ACBPS parameters that released insulin caused no detectable plasma membrane damage or cytotoxicity although temporary morphological changes could be observed immediately after ACBPS.

ACBPS did not alter the plasma membrane transmembrane potential, but did cause pronounced uptake of MitoTracker Red into the mitochondrial membrane, indicating an increased mitochondrial membrane potential. The ATP:ADP ratio following ACBPS did not change but guanosine triphosphate (GTP) levels increased and increased GTP levels have previously been associated with insulin release in INS-1 cells. These results provide evidence that, in the case of INS-1 cells, ACBPS promotes insulin release without causing cytotoxicity.

As background, some evidence suggests that the ACBPS waveform increases morbidity and mortality in a chronically-paced patient. In practice, electrical stimuli can be delivered as either monophasic or biphasic waveforms, and with anodal as well as cathodal polarities. In cardiac tissues and whole heart acute studies, ACBPS increases the speed of conduction and contractility. In addition, ACBPS may also promote healing of infarcts as judged by improved chronic hemodynamics.

In isolated cell studies, biphasic stimulation may be more advantageous than monophasic stimulation since it generates lower levels of electrolysis products at the electrodes and thus can be applied for longer time periods and at higher voltages. Stimulation with biphasic waveforms in which the initial phase is anodal (ACBPS) stimulate only at the end of the initial anodal pulse, coincident with the start of the cathodal phase. In cellular studies, ACBPS stimulation has been shown to elicit effects that differ from those induced by monophasic pulses.

Pancreatic beta cells are electrically-active and have similar ion channels to those found on cardiac myocytes but lack contractile elements. Pancreatic beta cells are thus an alternative cell model to investigate the effects of electrical stimulation on plasma membrane-dependent activities. These cells have been used extensively to study the glucose-stimulated insulin secretion (GSIS) pathway, which is regulated, at least in part, by plasma membrane voltage-dependent ion channels. The canonical GSIS pathway involves the uptake of glucose and consequential production of ATP. An increase in intracellular ATP results in the closure of ATP-sensitive potassium channels in the plasma membrane, leading to membrane depolarization and activation of voltage-sensitive calcium channels. The influx of calcium into the cell promotes the fusion of insulin-containing vesicles with the plasma membrane and, thereby, the subsequent release of insulin. A role for ion channels in insulin secretion from beta cells, therefore, is well established. However, ATP-independent mechanisms of GSIS have also been identified and mitochondrial GTP has been characterized as a critical signal for insulin secretion.

It is thought that electrical currents, including ACBPS, have the potential to alter the electronic flux of the plasma membrane of pancreatic beta cells and modulate insulin release either by promoting or inhibiting the actions of plasma membrane ion channels. The results described below explore the manner in which ACBPS can induce insulin secretion from rat insulinoma cells.

Materials and Methods
Cells

A rat insulinoma cell line INS-1 was obtained and were grown in 6-well polystyrene culture plates as attached monolayers in RPMI1640 culture medium supplemented with 10% fetal bovine serum, 10 mM HEPES, 1 mM sodium pyruvate, 2 mM L-glutamine, 0.05 mM 2-mercaptoethanol, 100 IU/mL penicillin and 100 µg/mL streptomycin (i.e., complete medium). Cells were maintained and experiments were conducted in a humidified atmosphere of 5% $CO_2$ in air at 37° C. Select studies were carried out in glucose-free RPMI1640 culture medium supplemented with reagents as described above. In these experiments, the regular medium was exchanged for glucose-free medium 16 hours prior to the electrical stimulation experiment.

Reagents

Antimycin A, oligomycin A, verapamil, nifedipine, valinomycin and gramicidin A were obtained from Santa Cruz Biotechnology and dissolved in dimethyl sulfoxide (DMSO). Mitotracker Red CMXRos and $DiBac_4(3)$ were obtained from ThermoFisher Scientific, and 3-(4,5-dimethylthiazol-2-yl)-2,5-diphenyltetrazolium bromide (MTT) was obtained from Research Products International.

Electrical Stimulation

ACBPS was applied to cells using a C-Pace EP cell culture stimulator in combination with a C-dish electrode array for a 6-well plate. Control cells were mock stimulated using an identical 6-well C-dish electrode array that was not connected to the stimulator. Unless otherwise stated, the biphasic stimulation parameters were anodal followed by cathodal at 10 Hz (frequency), 5 milliseconds (ms) (total pulse duration), and 25 V (pulse magnitude).

Figure 4B:
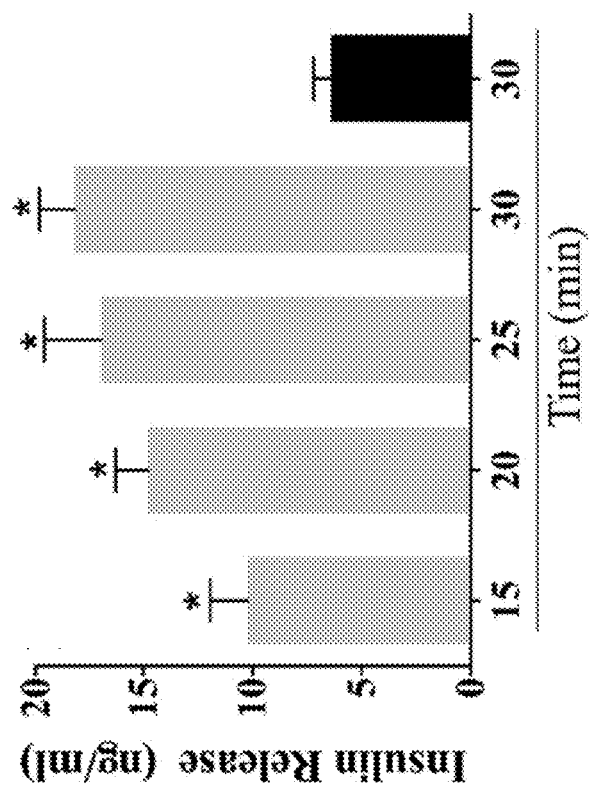
FIG. 4B is a graphical representation of insulin release as a function of time during a 25 volt pulse magnitude, according to an exemplary embodiment of the present disclosure.
Figure 4A:
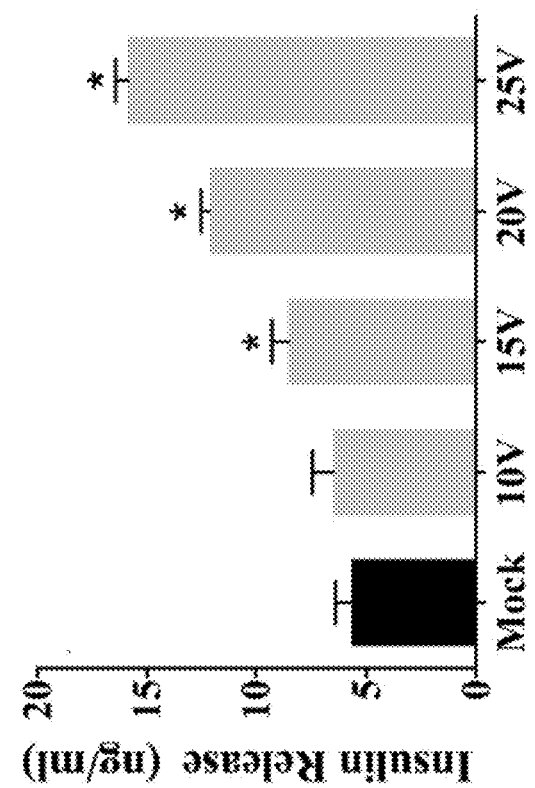
FIG. 4A is a graphical representation of insulin release as a function of pulse magnitude, according to an exemplary embodiment of the present disclosure.

For instance, as it relates to the insulin release study of FIG. 4A, ACBPS may be applied at variable voltages of between 10 V and 25 V (pulse magnitude). And, as it relates to the release study of FIG. 4B, ACBPS may be applied at 25 V (pulse magnitude) and in 5 ms pulse durations over a period of between 15 minutes and 30 minutes, a control being maintained for a period of 30 minutes without electrical stimulation in the form of ACBPS to evaluate a baseline of insulin release.

Insulin Release

Insulin release from INS-1 cells into the culture medium was determined by ELISA (Rat Insulin ELISA Kit) per the manufacturer's instructions. For these studies, cells were grown to approximately 95% confluency in 6-well plates containing 3 mL complete medium/well. 16 hours before stimulation, the medium was replaced with 3 mL fresh complete medium. Immediately prior to stimulation, the medium was aspirated, the cells were washed twice with 2 mL phosphate buffered saline (PBS), and then 3 mL fresh complete medium was added to each well. Cells were subjected to ACBPS (10 Hz, (2.5 ms)/(2.5 ms) pulse duration (i.e. anodal duration/cathodal duration), 10-25 V magnitude) or mock stimulation for the indicated times. At the end of the stimulation periods, a 0.5 mL sample of medium was removed from each well and stored frozen at −70° C. for later analysis. In some studies, cells were grown for 16 hours in glucose-free medium prior to stimulation. To examine a role for electrolysis products in promoting insulin release, an additional series of experiments were conducted that involved the application of ACBPS (10 Hz, (2.5 ms)/(2.5 ms) pulse duration, 25 V magnitude) or no stimulation (mock) for 30 min to 6-well plates containing only complete medium (3 mL per well) (i.e., no cells). At the end of the stimulation period, the "pre-stimulated" medium was transferred to cells that had been washed twice with PBS (as above). The cells were allowed to incubate with the pre-stimulated medium for 30 min, after which a 0.5 mL sample of medium was removed from each well and stored frozen at −70° C. for latter analysis. The insulin concentration of the culture medium was measured by colorimetric ELISA using 2 µL of the culture medium as described by the manufacturer. Culture medium samples and insulin standards were allowed to bind for 16 hours at 4° C. The concentration of insulin in each medium sample was estimated by interpolation on a standard curve (0.156-10 ng/mL) obtained using purified recombinant rat insulin provided in the ELISA kit.

Insulin release from INS-1 cells was also confirmed by immunostaining for intracellular insulin. In these studies, INS-1 cells were grown to 95% confluency on 18 mm glass coverslips. The coverslips were washed twice with 2 mL PBS, then placed in the well of a 6-well plate containing 3 mL per well complete medium and subjected to mock stimulation or ACBPS (10 Hz, (2.5 ms)/(2.5 ms) pulse duration, 25 V magnitude) for 30 min. Immediately following the stimulation period, the medium was aspirated, the coverslips rinsed twice with 2 mL of PBS, and then incubated in 2 mL freshly-prepared 3.7% (v/v) formaldehyde in PBS for 15 min at 25° C. (to fix the cells). The cells were permeabilized by incubation of the coverslips in 2 mL 0.1% (v/v) Triton X100 in PBS for 10 min at 25° C., and subsequently incubated in 2 mL blocking buffer (RPMI1640 containing 10% fetal bovine serum diluted 1:1 with 10 mM Tris-HCl, pH 7.8, 150 mM NaCl and 0.2% Tween-20 (TBST)). Rabbit anti-insulin antibody (Abcam, #ab63820), diluted 1:1000 in 2 mL blocking buffer, was added to each coverslip and allowed to incubate for 16 hours at 4° C. The coverslips were rinsed extensively in TBST prior to incubation with Alexa Fluor-488-conjugated goat anti-rabbit IgG secondary antibody diluted 1:1000 in 2 mL blocking buffer containing 1 μg/mL DAPI (MilliporeSigma, Burlington, MA) for 30 min at 25° C. In some experiments, phalloidin (1 μg/mL, phalloidin CruzFluor 555 conjugate) was added to blocking buffer containing secondary antibodies and DAPI. Following the addition of the secondary antibody, the cells were rinsed extensively with TBST, dipped in deionized-distilled $H_2O$, inverted, and then mounted on a glass slide. Cells were visualized at 600× magnification using a Nikon C-1 confocal microscope.

Cytotoxicity

Plasma membrane integrity and cytotoxicity were assessed in INS-1 cells using Trypan blue staining. Cells were grown to 95% confluency in 6-well plates and then underwent mock stimulation or ACBPS (10 Hz, (2.5 ms)/(2.5 ms) pulse duration, 25 V magnitude) for 30 min. Immediately following the stimulation period, the medium was aspirated and 1 mL trypsin solution (0.25% trypsin; 0.1% EDTA) was added to each well. After 30 s, 2 mL complete medium was added to each well, the cells were dislodged, transferred to a 15 mL Falcon tube and collected by centrifugation (800 rpm for 4 min). The cell pellet was suspended in 1 mL Hank's balanced salt solution (containing $Ca^+$ and $Mg^{++}$, Invitrogen), gently vortexed, and a 50 μL aliquot was transferred to a 1.7 mL microfuge tube containing 50 μl 0.4% Trypan blue solution. The cells were then gently mixed and 10 μL of the cell suspension was applied to a hemocytometer. One hundred cells were counted and the percentage of Trypan blue-positive cells was determined. In addition, Trypan blue staining was conducted 4 hours after the end of the stimulation period. In these experiments, cells underwent mock stimulation or ACBPS (10 Hz, (2.5 ms)/(2.5 ms) pulse duration, 25 V magnitude) for 30 min. At the end of the stimulation period the medium was replaced with 3 mL per well of fresh complete medium, and the cells were placed in a cell incubator for 4 hours. The cells were collected, stained with Trypan blue and analyzed as described above.

Cytotoxicity was also examined using the intracellular reduction of MTT. INS-1 cells were grown to 95% confluency in 6-well plates, and then underwent mock stimulation or ACBPS (10 Hz, (2.5 ms)/(2.5 mc) pulse duration, 25 V magnitude) for 30 min. Immediately following the stimulation period, the medium in each well was replaced by 3 mL fresh complete medium containing MTT (1 mg/mL) for 15 min. The MTT-containing medium was then aspirated and the cells were solubilized by the addition of DMSO (1 mL per well). After agitation of the 6-well plates on an orbital shaker for 10 min, 100 μL aliquots from each well were transferred to a 96-well plate and the absorbance was determined in triplicate at a wavelength of 550 nm using a Thermo Max microplate reader.

Transmembrane Potential Assay

The transmembrane potential (TMP) was estimated using $DiBAC_4(3)$ staining as previously described. For these studies, INS-1 cells were grown to 95% confluency in 6-well plates. The medium was aspirated, replaced with 3 mL fresh complete medium per well, and subjected to mock stimulation or ACBPS (10 Hz, (2.5 ms)/(2.5 ms) pulse duration, 25 V magnitude) for 30 min. Immediately following the stimulation period, the medium was aspirated from each well and replaced with 2 mL per well staining buffer (20 mM HEPES, 120 mM NaCl, 2 mM KCl, 2 mM $CaCl_2$, 1 mM $MgCl_2$, and 5 mM glucose [pH 7.4]) containing 5 μM $DiBAC_4(3)$ with DMSO (mock and ACBPS), valinomycin (100 nM), gramicidin (100 nM) or KCl (140 mM). The cells were allowed to incubate in staining buffer at 37° C. for 30 min. Thereafter, the fluorescence intensity of $DiBAC_4(3)$ stained INS-1 cells (Ex 490 nm/Em 516 nm) was measured using a BioTek Synergy H1 plate reader programmed to acquire 49 (7×7) individual measurements per well.

MitoTracker Red Staining

The effect of ACBPS stimulation on the inner mitochondrial membrane potential in cells was examined using MitoTracker Red staining. For these studies, cells were grown to 95% confluency on 18 mm glass coverslips, then placed in a 6-well dish containing 3 mL complete medium and subjected to mock stimulation or ACBPS (10 Hz, (2.5 ms)/(2.5 ms) pulse duration, 25 V magnitude) for 30 min. At the indicated times after the stimulation period, the medium was aspirated, and 100 nM MitoTracker Red CMXRos (diluted in 3 mL complete medium) was added to each coverslip and incubated for 15 min at 37° C. The coverslips were then rinsed twice with 2 mL PBS, and subsequently fixed by incubation with 2 mL freshly-prepared 3.7% (v/v) formaldehyde in PBS for 15 min at 25° C. The coverslips were washed twice in 2 ml PBS and the cells were then permeabilized by incubation with 2 mL 0.1% (v/v) Triton X100 in PBS for 10 min at 25° C. The coverslips were then rinsed twice with 2 mL PBS, and subsequently incubated with 2 mL fresh PBS containing 1 μg/mL DAPI for 5 min at 25° C. The coverslips were washed twice in 2 mL PBS, rinsed once in deionized-distilled $H_2O$, and mounted on a glass slide. For studies combining MitoTracker Red staining and insulin immunostaining, cells were fixed, permeabilized, blocked and immunostained for insulin (as described above) after incubation with MitoTracker Red. Cells were visualized at 600× magnification using a Nikon C-1 confocal microscope.

Cellular Respiration

Oxygen consumption was measured in INS-1 cells after ACBPS. Cells, grown to 95% confluency in 6-well plates, underwent mock stimulation or ACBPS (10 Hz, (2.5 ms)/(2.5 ms) pulse duration, 25 V magnitude) for 30 min. Immediately following the stimulation period, the medium was aspirated and replaced with 3 mL fresh complete medium. At the indicated times after stimulation, the cells were gently dislodged, transferred to a 15 mL Falcon tube, and pelleted at 800 rpm for 4 min. The cell pellet was suspended in 12 mL fresh complete medium at 37° C., cell number was determined using a hemocytometer, and 3 mL aliquots were assayed for oxygen consumption using a YSI Biological Oxygen Monitor. Cellular oxygen uptake was measured over a 15 min period and the rate of oxygen consumption was calculated from 5 min to 15 min. Calculations of dissolved oxygen were corrected for temperature (37° C.) and pressure (29.9 mmHg).

Intracellular Nucleotides

Nucleotide concentrations in INS-1 cells were determined by LC-MS analysis. Cells, grown to 95% confluency in 6-well plates (in duplicate), underwent mock stimulation or ACBPS (10 Hz, (2.5 ms)/(2.5 ms) pulse duration, 25 V magnitude) for 30 min. Immediately following the stimulation period, the medium was aspirated, the cells washed twice with PBS, and subsequently lysed with 500 μL ice-cold 70% methanol in water containing 20 μL internal standard and vortexed for 10 sec. The resulting extract was centrifuged at 8000×g for 5 min at 4° C. The resulting supernatant was transferred to a new centrifuge tube and stored on ice. The remaining pellet was suspended in 500 μL ice-cold methanol by vortexing for 10 sec. The suspension was then centrifuged at 8000×g for 5 min at 4° C. The supernatant was removed and combined with the 70% methanol supernatant which was then centrifuged at 18,000×g for 15 min. The resulting supernatant was transferred to a new tube and dried in a vacuum centrifuge at 55° C. Each dried sample was reconstituted in 100 μL 50% methanol in water and centrifuged at 18,000×g for 10 min at 4° C. Samples were separated high performance liquid chromatography (HPLC) using a 100×2 mm 5 μm Luna $NH_2$ column operated in HILIC mode. Mass spectrometric analysis was performed on a triple quadrupole mass spectrometer in positive ionization mode. The drying gas was 300° C. at a flow rate of 12 mL per min. The nebulizer pressure was 30 psi. The capillary voltage was 4000 V. Results were quantified using calibration curves to obtain the on-column concentration, followed by normalization of the results to protein concentration. Protein concentrations were determined using cell homogenates obtained from duplicate plates of cells treated with Mock stimulation or ACBPS.

Results

As shown in FIG. 4A in FIG. 4B, ACBPS of INS-1 cells resulted in an increase in insulin release into the culture medium that was pulse amplitude (FIG. 4A) and stimulation period-dependent (FIG. 4B).

Figure 5B:
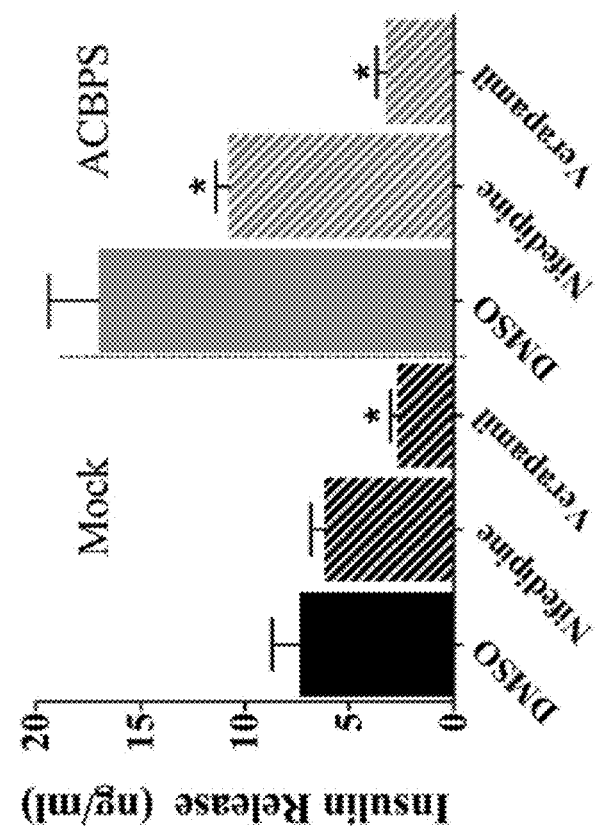
FIG. 5B is a graphical representation of insulin release as a function of electrical stimulation and in view of calcium channel blockers, according to an exemplary embodiment of the present disclosure.
Figure 5A:
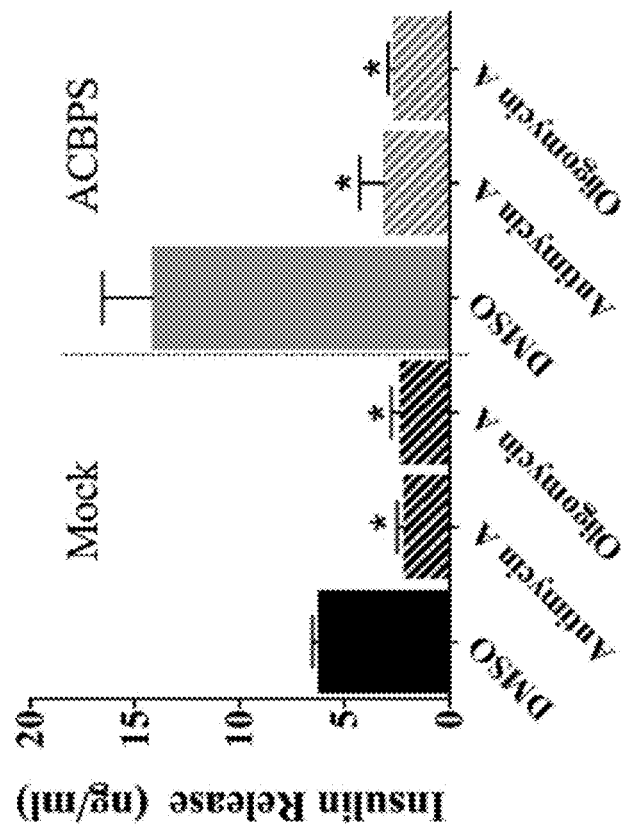
FIG. 5A is a graphical representation of insulin release as a function of electrical stimulation and in view of mitochondrial poisons, according to an exemplary embodiment of the present disclosure.

With reference to FIG. 5A and FIG. 5B, basal insulin release was inhibited by the mitochondrial poisons antimycin A and oligomycin A (FIG. 5A) and by the calcium channel blocker verapamil (FIG. 5B). ACBPS-induced insulin release was also inhibited by the mitochondrial poisons antimycin A or oligomycin A, as shown in FIG. 5A, and by both calcium channel blockers, verapamil and nifedipine, as shown in FIG. 5B.

Figure 6A:
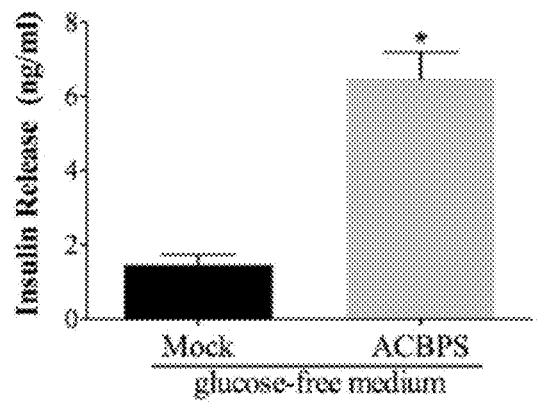
FIG. 6A is a graphical representation of insulin release as a function of electrical stimulation and in view of glucose-free medium, according to an exemplary embodiment of the present disclosure.
Figure 6B:
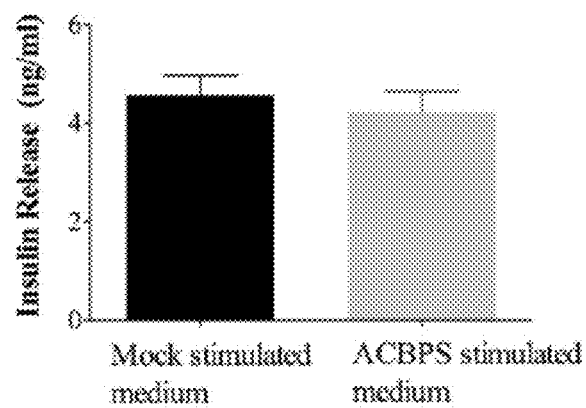
FIG. 6B is a graphical representation of insulin release as a function of stimulated culture medium, according to an exemplary embodiment of the present disclosure.

With reference to FIG. 6A and FIG. 6B, basal insulin release from INS-1 cells was reduced when cells were grown and mock stimulated in glucose-free medium (e.g., compare mock of FIG. 6A with mock of FIG. 6B). Under similar glucose-free conditions, ACBPS continued to stimulate insulin release, as shown in FIG. 6A. No increase in insulin release was observed when INS-1 cells were exposed to culture medium previously subjected to ACBPS, as shown in FIG. 6B, indicating that the insulin release observed during ACBPS does not result from electrolysis products generated from the tissue culture medium.

Figure 6C:
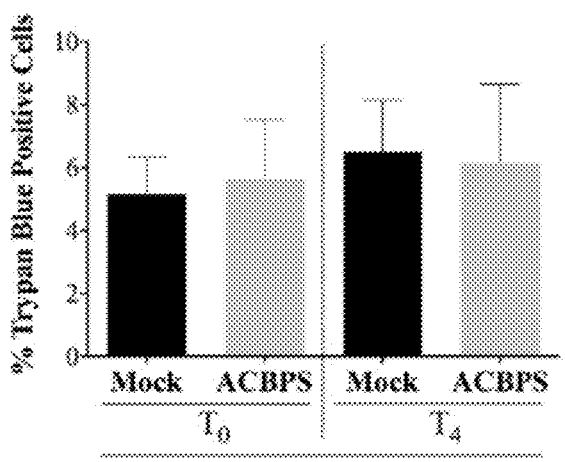
FIG. 6C is a graphical representation of cellular viability as a function of electrical stimulation, according to an exemplary embodiment of the present disclosure.
Figure 6D:
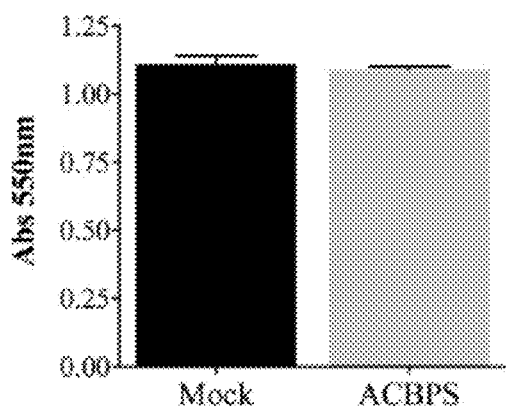
FIG. 6D is a graphical representation of cell metabolism as a function of electrical stimulation, according to an exemplary embodiment of the present disclosure.

With reference to FIG. 6C and FIG. 6D, and in view of FIG. 5A and FIG. 5B, data indicating the requirement of mitochondrial activity and calcium channels for insulin release clearly demonstrated that ACBPS was not causing insulin release as a result of toxicity. We confirmed that ACBPS did not increase Trypan blue uptake by INS-1 cells measured immediately or 4 hours after the stimulation period, as shown in FIG. 6C. Similarly, ACBPS did not affect MTT-formazan production measured immediately following the stimulation period, as shown in FIG. 6D. While ACBPS did not cause plasma membrane damage (see Trypan blue assay) or cell loss (see MTT assay), a temporary change in cell morphology was observed immediately after ACBPS. Specifically, INS-1 cells subjected to ACBPS appeared to temporarily lose contact with their neighboring cells but did not detach from the coverslip.

Figure 7A:
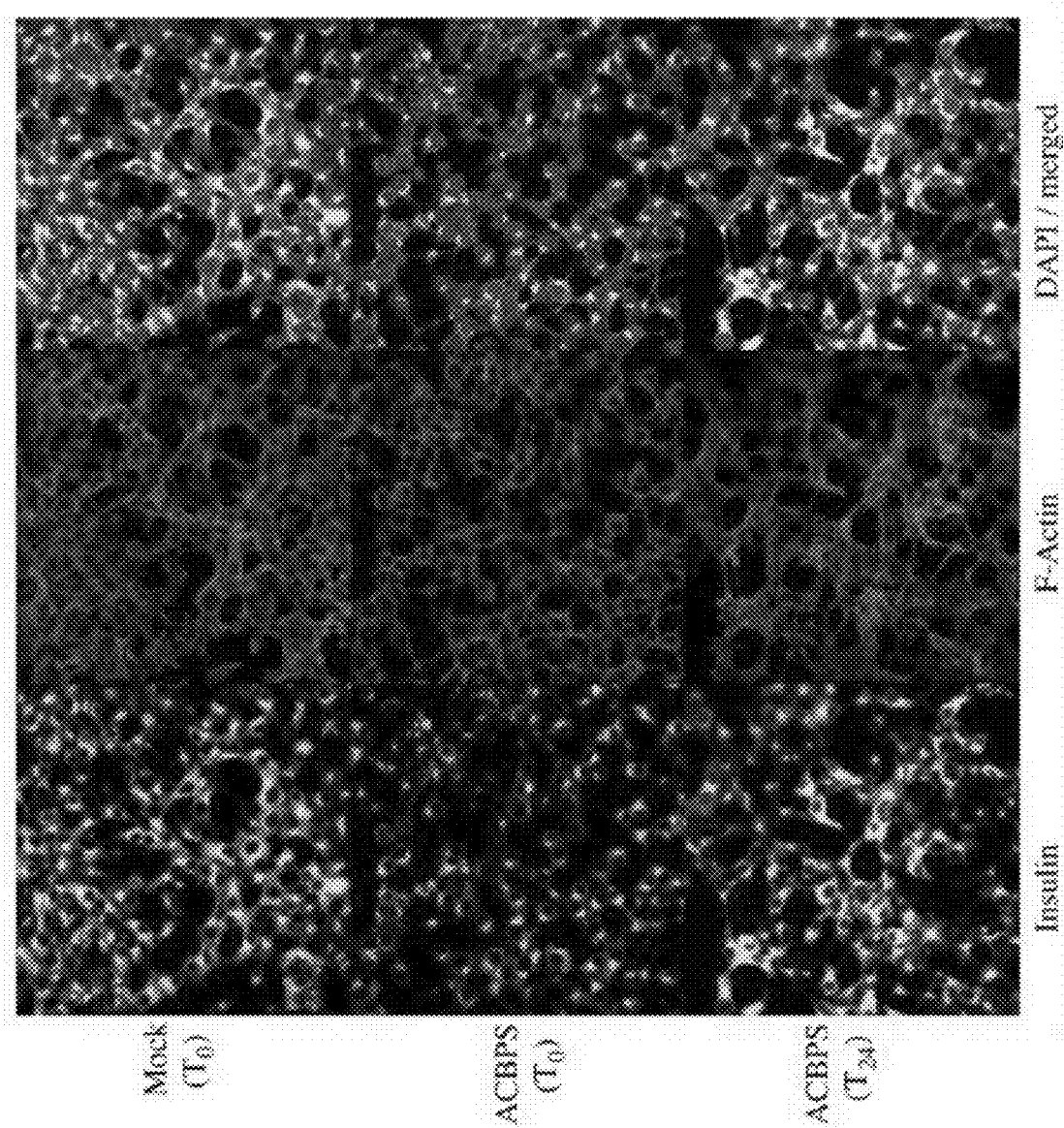
FIG. 7A is an illustration of the effects of electrical stimulation on intracellular insulin levels and cell morphology, according to an exemplary embodiment of the present disclosure.
Figure 7B:
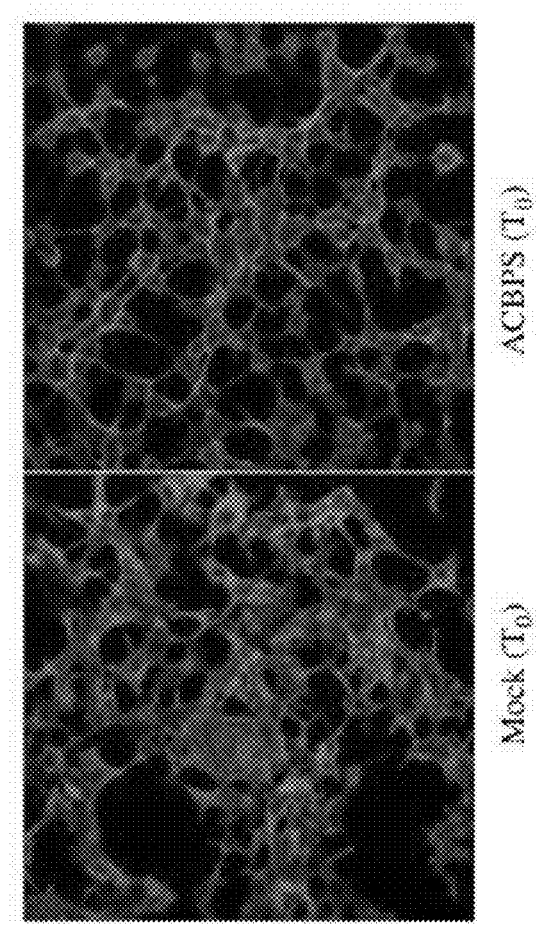
FIG. 7B is an illustration of the effects of electrical stimulation on intracellular insulin levels and cell morphology, according to an exemplary embodiment of the present disclosure.

This change in cell-to-cell contact induced by ACBPS was confirmed by immunocytochemical studies which showed the phenomenon occurring immediately after the stimulation period (To) and recovering 24 hours (T24) after stimulation (FIG. 4). In these studies, INS-1 cells were also examined for insulin content by immunostaining and these data, shown in FIG. 7A and FIG. 7B, confirmed the ELISA results in showing a reduced level of intracellular insulin staining immediately following ACBPS and recovery of insulin levels 24 hours, thereafter, relative to cells that underwent mock stimulation.

Figure 8A:
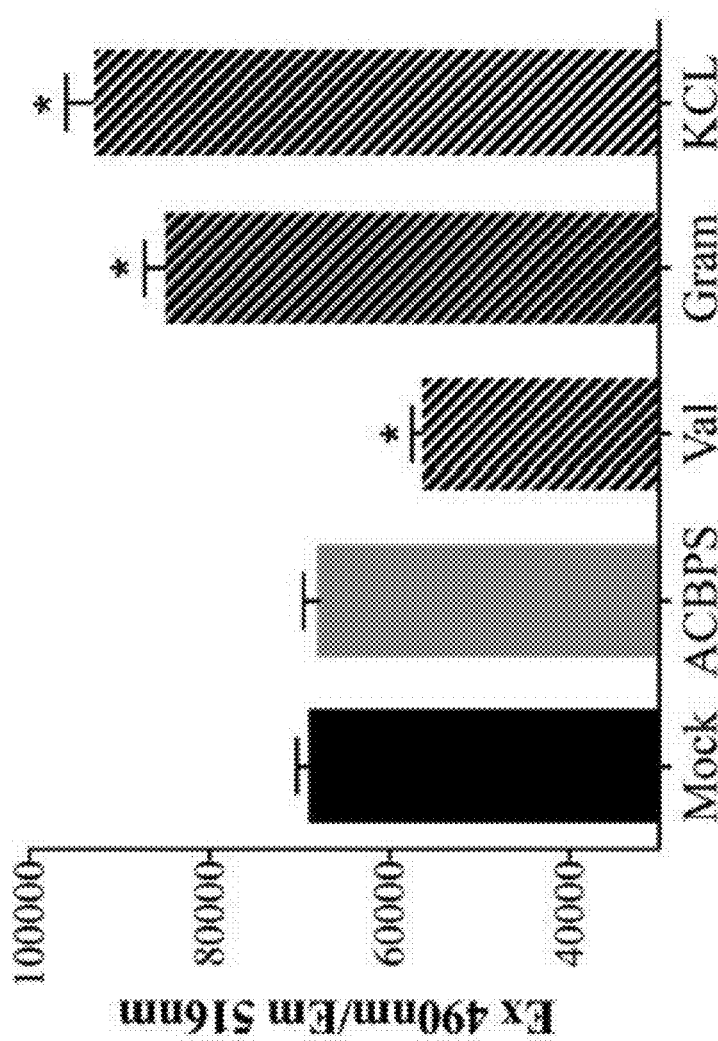
FIG. 8A is a graphical representation of the effects of electrical stimulation on the plasma membrane transmembrane and inner mitochondrial membrane potentials, according to an exemplary embodiment of the present disclosure.

To determine if the effects of ACBPS were mediated by changes in the plasma membrane potential, $DiBAC_4(3)$ dye uptake and fluorescence was measured in INS-1 cells subjected to ACBPS. This anionic dye accumulates in the plasma membrane of depolarized cells but is excluded from the plasma membrane of hyperpolarized cells. As shown in FIG. 8A, cells exposed to ACBPS did not show any increase in $DiBAC_4(3)$ fluorescence relative to mock stimulation cells. To validate the utility of $DiBAC_4(3)$ as a tool to estimate changes in plasma membrane potential, control experiments were also conducted in INS-1 cells treated with valinomycin (control for plasma membrane hyperpolarization), or with gramicidin or KCl (positive controls for plasma membrane depolarization). As expected, with continued reference to FIG. 8A, valinomycin induced a decrease in $DiBAC_4(3)$ fluorescence while gramicidin and KCl elicited increased $DiBAC_4(3)$ fluorescence.

Figure 8B:
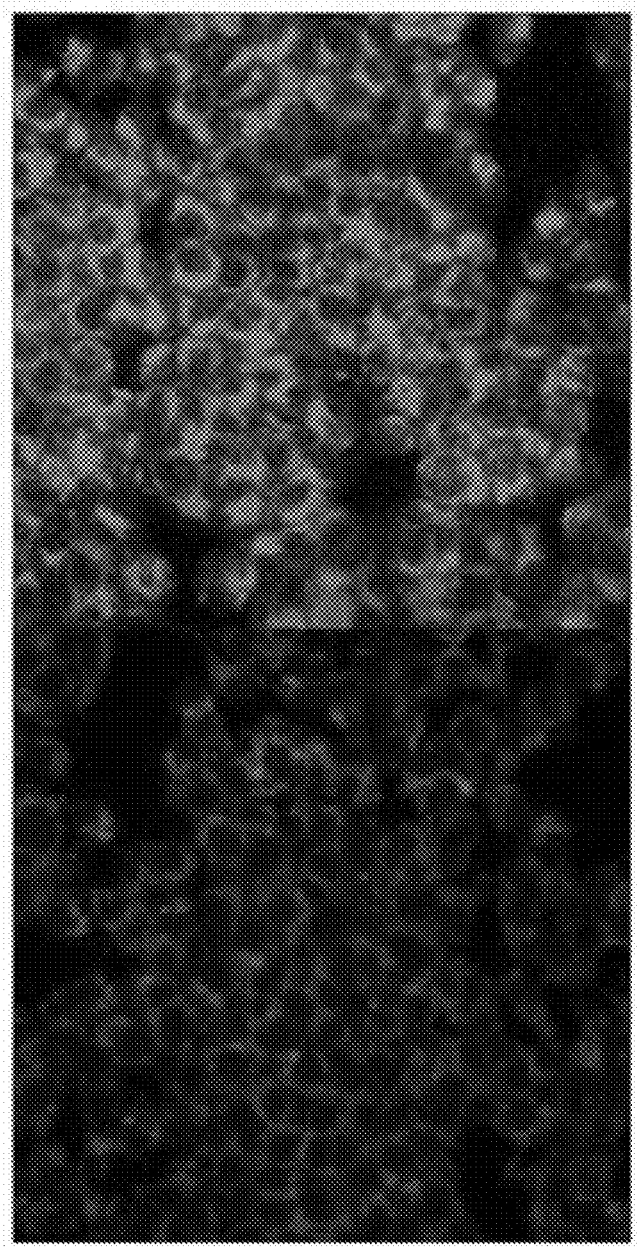
FIG. 8B is an illustration of the effects of electrical stimulation on inner mitochondrial membrane potentials, according to an exemplary embodiment of the present disclosure.
Figure 9A:
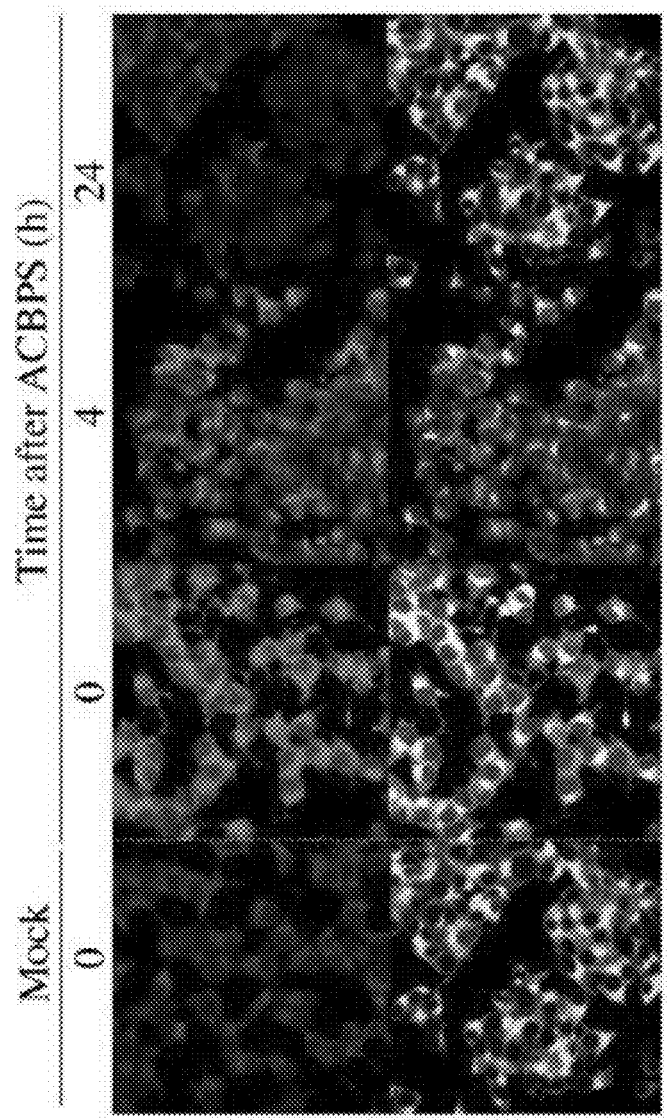
FIG. 9A is an illustration of the effects of electrical stimulation on mitochondrial membrane potentials and insulin release, according to an exemplary embodiment of the present disclosure.

Because mitochondria play a central role in regulating insulin release from pancreatic beta cells, ACBPS-induced changes in the mitochondrial inner membrane potential of INS-1 cells were examined using MitoTracker Red staining. In these studies, shown in FIG. 8B and FIG. 9A, ACBPS induced a dramatic increase in the intensity of MitoTracker Red staining immediately following the stimulation period. The increase in MitoTracker Red staining of INS-1 cells was long lived, as shown in FIG. 9A, with increased staining being observed 4 hours after the stimulation period. MitoTracker Red staining returned to mock stimulation levels by 24 hours. In these same studies the levels of intracellular insulin decreased immediately following ACBPS, were still depressed at 4 hours, but returned to normal after 24 hours post stimulation.

Figure 9B:
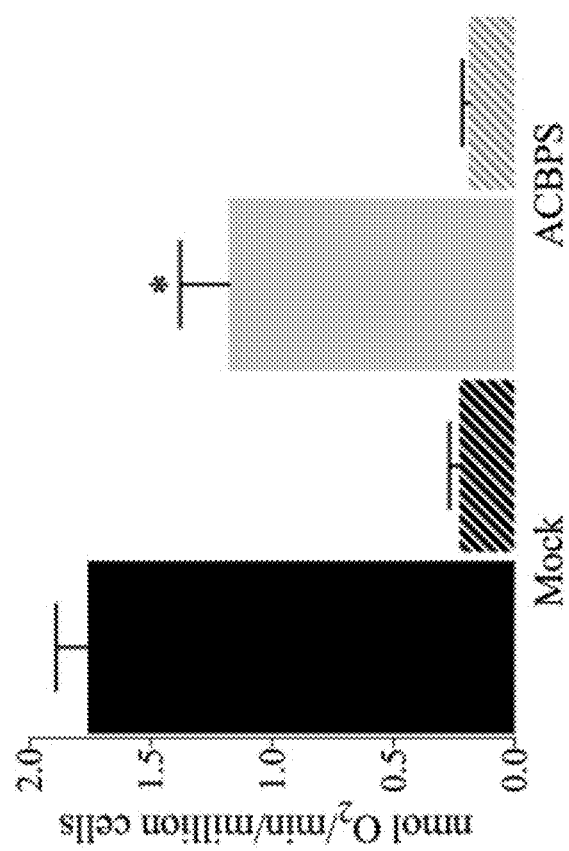
FIG. 9B is a graphical representation of cellular respiration in the absence and presence of mitochondrial poisons, according to an exemplary embodiment of the present disclosure.

To further examine the effect of ACBPS on mitochondrial function in INS-1 cells, cellular respiration was measured, as shown in FIG. 9B. In these experiments, cells subjected to ACBPS demonstrated a decrease in cellular respiration and, similar to MitoTracker Red staining, the decrease in oxygen consumption was detectable immediately after ACBPS, returning to mock stimulation levels by 24 hours after ACBPS.

Figure 9C:
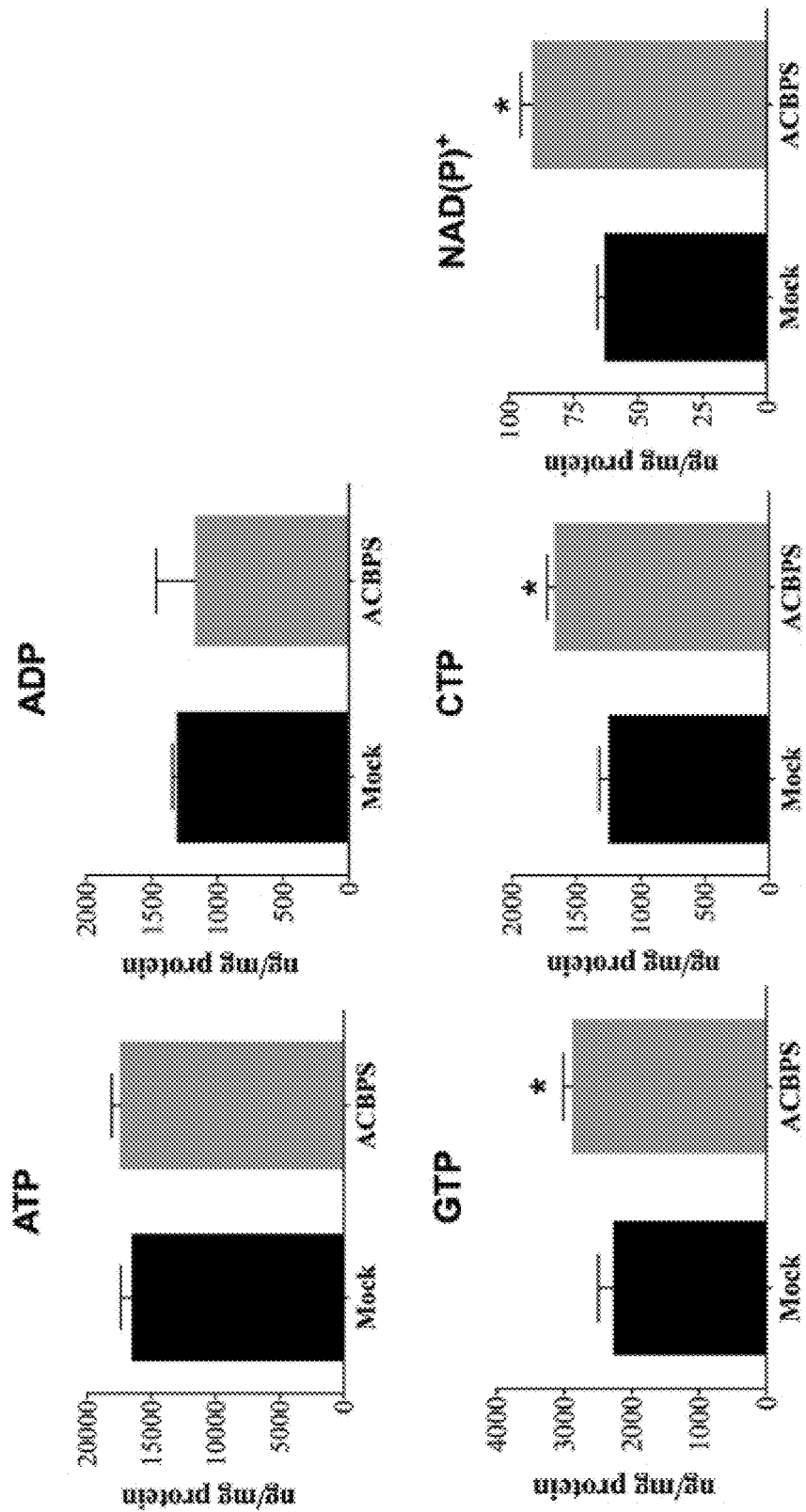
FIG. 9C is a panel of graphical representations of the effects of electrical stimulation on quantities of adenosine triphosphate, adenosine diphosphate, guanosine triphosphate, cytidine triphosphate, and nicotinamide adenine dinucleotide phosphate, according to an exemplary embodiment of the present disclosure.

Given the importance of cellular nucleotides in controlling insulin secretion from beta cells, the impact of ACBPS on intracellular levels of critical nucleotides (including ATP and GTP) were analyzed in FIG. 9C. ACBPS did not alter ATP but did significantly increase cellular GTP levels. Stimulation also increased the intracellular levels of CTP and $NAD(P)^+$. ACBPS did not change ($\alpha=0.05$) intracellular levels of adenosine, AMP, cytidine, CMP, CDP, guanosine, GMP, GDP, uridine, UMP, UDP, UTP, FAD, NADH or $NAD^+$.

Analysis

In these studies, ACBPS was shown to increase the rate of insulin release from INS-1 cells in a manner that was dependent on the pulse magnitude and time period of stimulation. ACBPS-induced insulin release occurred in the absence of glucose, excluding the possibility that the secretion of insulin involved the increased cellular uptake of glucose. The amounts of insulin released by INS-1 cells during ACBPS were similar to those shown to be induced by glucose, the physiological stimulus for insulin secretion. Both basal and ACBPS-induced insulin release were inhibited by antimycin A, oligomycin A, nifedipine and verapamil, indicating roles for mitochondria and calcium channels in the release process. These results argue against the possibility that ACBPS was eliciting insulin release by non-specific damage to the plasma membrane of the cell. The Trypan blue and MTT assay results also demonstrate that ACBPS did not compromise the plasma membrane or induce adverse cytotoxicity to INS-1 cells.

As described, insulin release from beta cells is dependent upon plasma membrane depolarization and the opening of voltage-dependent calcium channels. To further examine the mechanism by which ACBPS promoted insulin release, the capacity of ACBPS to alter the INS-1 transmembrane potential was examined using the slow-responsive dye $DiBAC_4$(3). With regard to INS-1 cells, ACBPS had no effect on transmembrane potential at the end of the stimulation period. This would suggest that any changes to the transmembrane potential that ACBPS may cause during stimulation rapidly resolve once stimulation is completed. While ACBPS did not change the plasma membrane transmembrane potential after ACBPS, a pronounced increase in MitoTracker Red staining of the mitochondria was observed in INS-1 cells following ACBPS, an effect that extended for 4 hours beyond the end of the stimulation period. MitoTracker Red is a cationic dye that targets the negatively-charged inner mitochondrial membrane and can be used to approximate the electrical potential of the inner mitochondrial membrane. Therefore, increased staining with this dye may be reflective of a more hyperpolarized inner mitochondrial membrane. A strong association exists between mitochondrial membrane hyperpolarization and insulin secretion in pancreatic beta cells. The metabolic conversion of glucose to ATP induces mitochondrial hyperpolarization, increases cellular respiration, and, when combined with an increase in the ATP:ADP ratio, promotes insulin release. Given the changes in mitochondrial activity observed using MitoTracker Red, alterations in the levels of ATP and ADP might have been expected. However, the increase in insulin release induced by ACBPS occurred without any detectible changes in the levels of ATP or ADP. Increased levels of GTP after ACBPS were detected however and this may have relevance for the insulin secretion observed. GTP generated in the mitochondria has been found to regulate insulin secretion in INS-1 cells and in cultured rat islets. siRNA suppression of the GTP producing pathway in INS-1 cells reduced glucose stimulated insulin secretion by 50% in a mechanism involving increases in cytosolic calcium levels.

INS-1 cells subjected to ACBPS unexpectedly exhibited decreases in oxygen consumption both immediately and 4 hours after the end of the stimulation period. This would suggest that ACBPS may alter the metabolic pathways within the beta cell, potentially to make it more oxygen-efficient. Interestingly, the time-course of the change in oxygen consumption appeared to parallel the changes in MitoTracker Red staining in being present immediately after stimulation, but not 24 hours after stimulation.

The exact mechanism by which ACBPS results in mitochondrial hyperpolarization and increased insulin release remains to be fully established. Given the inhibitory effects of verapamil and nifedipine, it is apparent that the release of insulin by ACBPS involves L-type calcium channels. It is thought that by promoting activation of these channels by transient depolarization of the plasma membrane, ACBPS will elicit insulin release from INS-1 cells. The consequent inward flux of calcium into the cytosol can trigger the mobilization of calcium from mitochondrial storage sites and lead to a more negative inner mitochondrial membrane potential. The changes in the morphology of INS-1 cells induced by ACBPS can also be the result of an increase in intracellular free calcium.

ACBPS of INS-1 cells results in increased insulin release, which is glucose-independent and not a result of plasma membrane damage or cytotoxicity. These data suggest that ACBPS may very well modulate the function of pancreatic beta cells in a manner quite separate from the usual canonical GSIS pathway and that electrical induction of endogenous insulin secretion may be valuable when the GSIS pathway is impaired in diseases such as diabetes.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) An apparatus for performing electrical current therapy on biological tissue, comprising at least one sensor, at least one electrode, and processing circuitry configured to acquire data from the at least one sensor, compare a value of the acquired data from the at least one sensor to a pre-determined threshold value, generate an electrical current based on the comparison of the value of the acquired data from the at least one sensor to the pre-determined threshold value, and apply the generated electrical current to the biological tissue via the at least one electrode, the applied generated electrical current corresponding to a voltage differential.

(2) The apparatus according to (1), wherein the generated electrical current is biphasic.

(3) The apparatus according to either (1) or (2), wherein the voltage differential corresponding to the applied generated electrical current is between 10 volts and 25 volts.

(4) The apparatus according to any one of (1) to (3), wherein the voltage differential corresponding to the applied generated electrical current is variable based on the comparison of the value of the acquired data from the at least one sensor to the pre-determined threshold value.

(5) The apparatus according to any one of (1) to (4), wherein the voltage differential corresponding to the applied generated electrical current is 25 volts.

(6) The apparatus according to any one of (1) to (5), wherein the biological tissue is a pancreas, the at least one sensor is an at least one glucose sensor, and the pre-determined threshold value is a blood glucose concentration associated with a healthy blood glucose concentration for a patient.

(7) The apparatus according to any one of (1) to (6), wherein the at least one electrode is positioned within a head of the pancreas via a common bile duct of the pancreas.

(8) The apparatus according to any one of (1) to (7), wherein the at least one sensor is an at least one voltage sensor and the pre-determined threshold value is a depolarization voltage of a membrane of the biological tissue.

(9) A method for performing electrical current therapy on biological tissue, comprising acquiring, by processing circuitry, data from at least one sensor, comparing, by the processing circuitry, a value of the acquired data from the at least one sensor to a pre-determined threshold value, generating, by the processing circuitry, an electrical current based on the comparison of the value of the acquired data from the at least one sensor to the pre-determined threshold value, and applying, by the processing circuitry, the generated electrical current to the biological tissue via at least one electrode, the applied generated electrical current corresponding to a voltage differential.

(10) The method according to (9), wherein the generating generates the electrical current as a biphasic electrical current.

(11) The method according to either (9) or (10), wherein the voltage differential corresponding to the applied generated electrical current is between 10 volts and 25 volts.

(12) The method according to any one of (9) to (11), wherein the voltage differential corresponding to the applied generated electrical current is variable based on the comparison of the value of the acquired data from the at least one sensor to the pre-determined threshold value.

(13) The method according to any one of (9) to (12), wherein the voltage differential corresponding to the applied generated electrical current is 25 volts.

(14) The method according to any one of (9) to (13), wherein the biological tissue is a pancreas, the at least one sensor is an at least one glucose sensor, and the pre-determined threshold value is a blood glucose concentration corresponding to a healthy blood glucose concentration for a patient.

(15) The method according to any one of (9) to (14), wherein the at least one sensor is an at least one voltage sensor and the pre-determined threshold value is a depolarization voltage of a membrane of the biological tissue.

(16) A non-transitory computer-readable storage medium storing computer-readable instructions that, when executed by a computer, cause the computer to perform a method for performing electrical current therapy on biological tissue, comprising acquiring data from at least one sensor, comparing a value of the acquired data from the at least one sensor to a pre-determined threshold value, generating an electrical current based on the comparison of the value of the acquired data from the at least one sensor to the pre-determined threshold value, and applying the generated electrical current to the biological tissue via at least one electrode, the applied generated electrical current corresponding to a voltage differential.

(17) The non-transitory computer-readable storage medium according to (16), wherein the generating generates the electrical current as a biphasic electrical current.

(18) The non-transitory computer-readable storage medium according to either (16) or (17), wherein the voltage differential corresponding to the applied generated electrical current is between 10 volts and 25 volts.

(19) The non-transitory computer-readable storage medium according to any one of (16) to (18), wherein the voltage differential corresponding to the applied generated electrical current is variable based on the comparison of the value of the acquired data from the at least one sensor to the pre-determined threshold value.

(20) The non-transitory computer-readable storage medium according to any one of (16) to (19), wherein the voltage differential corresponding to the applied generated electrical current is 25 volts.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for stimulating insulin release from pancreatic tissue within a pancreas, comprising:
    acquiring, by processing circuitry, data from at least one sensor;
    comparing, by the processing circuitry, a value of the acquired data from the at least one sensor to at least one pre-determined threshold value;
    generating, by the processing circuitry, a pulsed biphasic electrical current based on the comparison of the value of the acquired data from the at least one sensor to the at least one pre-determined threshold value; and
    applying the generated pulsed biphasic electrical current to the pancreatic tissue within a patient's pancreas via at least one electrode in an amount sufficient to elicit insulin release from pancreatic beta cells in the pancreatic tissue, wherein insulin release is increased from the pancreatic beta cells while increasing GTP levels in the pancreatic tissue.

2. The method according to claim 1, wherein the at least one sensor includes at least one glucose sensor, and the at least one pre-determined threshold value includes a blood glucose concentration associated with a healthy blood glucose concentration for a patient.

3. The method according to claim 2, wherein the at least one electrode is positioned within a head of the pancreas via a common bile duct of the pancreas.

4. The method according to claim 2, wherein the at least one sensor further includes an at least one voltage sensor and the at least one pre-determined threshold value corresponds to a depolarization voltage of a membrane of the pancreatic tissue.

5. The method of claim 1, wherein application of the generated pulsed biphasic electrical current to the pancreatic tissue is sufficient to cause transient depolarization of plasma cell membranes of the pancreatic tissue.

6. The method of claim 5, wherein the transient depolarization of the plasma membranes of the pancreatic tissue is sufficient to activate L-type calcium channels in the pancreatic tissue.

7. The method of claim 1, further comprising increasing the magnitude of the voltage of the pulsed biphasic electrical current in an amount sufficient to increase the rate of insulin release from the pancreatic beta cells.

8. The method of claim 1, further comprising increasing the time that the voltage of the pulsed biphasic electrical current is applied to the pancreatic tissue in an amount sufficient to increase the rate of insulin release from the pancreatic beta cells.

9. The method of claim 1, wherein insulin release is increased from the pancreatic beta cells while reducing oxygen consumption of the pancreatic tissue.

10. The method of claim 1, wherein insulin release is increased from the pancreatic beta cells without substantially damaging plasma membranes of the pancreatic tissue.

11. A non-transitory computer-readable storage medium storing computer-readable instructions that, when executed by a computer, cause the computer to perform a method for performing electrical current therapy on pancreatic tissue within a pancreas, the method comprising:
    acquiring data from at least one sensor;

comparing a value of the acquired data from the at least one sensor to a pre-determined threshold value;

generating an electrical current based on the comparison of the value of the acquired data from the at least one sensor to the pre-determined threshold value; and applying the generated pulsed biphasic electrical current to the pancreatic tissue within a patient's pancreas via at least one electrode in an amount sufficient to elicit insulin release from pancreatic beta cells in the pancreatic tissue, wherein insulin release is increased from the pancreatic beta cells while increasing GTP levels in the pancreatic tissue.

12. The non-transitory computer-readable storage medium according to claim 11, wherein the at least one pre-determined threshold value includes a blood glucose concentration associated with a healthy blood glucose concentration for a patient.

13. The non-transitory computer-readable storage medium according to claim 12, wherein the at least one pre-determined threshold value further includes a depolarization voltage of a membrane of the pancreatic tissue.

14. A system for performing electrical current therapy on pancreatic tissue within a pancreas, the system comprising:
at least one sensor and at least one electrode;
a controller operably coupled to the at least one sensor and the at least one electrode to:
acquire data from the at least one sensor;
compare a value of the acquired data from the at least one sensor to a pre-determined threshold value;
generate an electrical current based on the comparison of the value of the acquired data from the at least one sensor to the pre-determined threshold value; and
apply the generated pulsed biphasic electrical current to the pancreatic tissue within a patient's pancreas via the at least one electrode in an amount sufficient to elicit insulin release from pancreatic beta cells in the pancreatic tissue, wherein insulin release is increased from the pancreatic beta cells while increasing GTP levels in the pancreatic tissue.

15. The system according to claim 14, wherein the at least one sensor includes at least one glucose sensor, and the at least one pre-determined threshold value includes a blood glucose concentration associated with a healthy blood glucose concentration for a patient.

16. The system according to claim 14, wherein the at least one sensor further includes an at least one voltage sensor and the at least one pre-determined threshold value corresponds to a depolarization voltage of a membrane of the pancreatic tissue.

17. The non-transitory computer-readable storage medium according to claim 10, wherein insulin release is increased from the pancreatic beta cells while reducing oxygen consumption of the pancreatic tissue.

18. The system according to claim 14, wherein insulin release is increased from the pancreatic beta cells while reducing oxygen consumption of the pancreatic tissue.

* * * * *